United States Patent
Taguchi et al.

(10) Patent No.: US 6,656,229 B1
(45) Date of Patent: Dec. 2, 2003

(54) HAIR DYE AND HAIR-DYEING METHODS USING THE SAME

(75) Inventors: Kazumi Taguchi, Saitama-ken (JP); Takao Tokano, Saitama-ken (JP); Yoshio Yamaoka, Saitama-ken (JP); Kazumaro Furuse, Tokyo (JP)

(73) Assignees: Real Chemical Co., Ltd., Tokyo (JP); Yugen Kaisha Kusaki Kobo, Kanagawa-ken (JP)

(*) Notice: Subject to any disclaimer, the term of this patent is extended or adjusted under 35 U.S.C. 154(b) by 0 days.

(21) Appl. No.: 09/648,209

(22) Filed: Aug. 25, 2000

(30) Foreign Application Priority Data

Aug. 27, 1999 (JP) ............................................. 11-241841

(51) Int. Cl.[7] .................................................. A61K 7/13
(52) U.S. Cl. ................................ 8/405; 8/423; 424/701; 424/401
(58) Field of Search ................................. 424/70.1, 401; 8/405, 423

(56) References Cited

U.S. PATENT DOCUMENTS

| | | | | | |
|---|---|---|---|---|---|
| 5,078,750 A | * | 1/1992 | Komai et al. | ................... | 8/405 |
| 5,856,451 A | * | 1/1999 | Olsen et al. | ................... | 435/189 |
| 5,865,853 A | * | 2/1999 | Schmitt et al. | ................... | 8/405 |
| 5,965,114 A | * | 10/1999 | Braun et al. | ................... | 424/70.1 |
| 5,965,146 A | * | 10/1999 | Franzke et al. | ................... | 424/401 |
| 5,989,876 A | * | 11/1999 | Belcour-Castro et al. | ... | 435/117 |
| 6,121,243 A | * | 9/2000 | Lanzendorfer et al. | ....... | 428/59 |

FOREIGN PATENT DOCUMENTS

| | | | | |
|---|---|---|---|---|
| JP | 408165227 A | * | 12/1994 | ............. A61K/7/13 |
| JP | 10-53720 | | 2/1998 | |

* cited by examiner

Primary Examiner—Yogendra N. Gupta
Assistant Examiner—Eisa Elhilo
(74) Attorney, Agent, or Firm—Weingarten, Schurgin, Gagnebin & Lebovici LLP

(57) ABSTRACT

A hair dye and hair-dyeing methods using the hair dye are provided. The hair dye comprises, as essential ingredients, (i) a formulation primarily composed of a dye component including indican derived from indigo plants and (ii) a formulation primarily composed of a β-glucosidase enzyme component. Hair is first mordanted with a dye mordant such as aluminum, iron and the like, and then secondly the prepared hair dye is uniformly applied to the hair either directly or as a mixture of the dye and a proper amount of water. Upon completion of the hair-dyeing, hair is rinsed with water and is finished by drying.

16 Claims, 1 Drawing Sheet

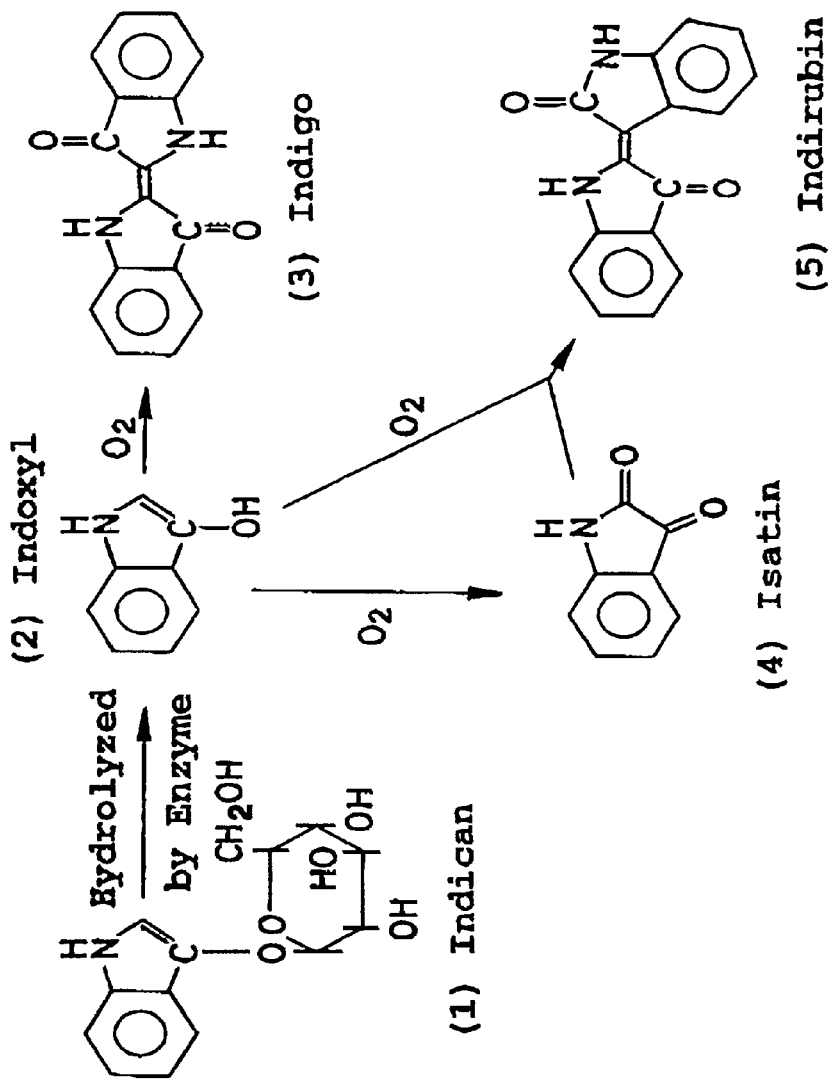

HAIR DYE AND HAIR-DYEING METHODS USING THE SAME

BACKGROUND OF THE INVENTION

1. Field of the Invention

The present invention generally relates to hair dyes and, more particularly, to a new hair dye using a fresh natural indigo leaf or a juice of a fresh natural indigo leaf. The present invention also relates to a method for dyeing hair using such dyes.

2. Description of the Prior Art

Conventionally, several compositions and methods for dyeing hair have been known. Examples of such a known hair dyeing dye include a synthesized hair dye using an oxidation dye which have a high hair-dyeing performance as well as a long-lasting performance, a plant-based hair dye which contains "henna" as its primary component and is widely used in Europe and in the US, and a hair dye commonly referred to as "hair manicure", to which an acid dye is blended.

Each of the known hair dyes is associated with certain drawbacks. Oxidation dyes are known to cause allergies in humans. The "henna" dye has a limited variation in color and does not go well with the black hair of the Japanese. Some allergic events are also reported for the dye. Acid dyes have a low durability since the dyes are just soaked up by the hair. Some of the conventional hair-dyeing agents are known to stain skin when spilt onto skin.

A hair dye is proposed in Japanese Patent Laid-open Publication No. Hei 10-53720 which is made by emulsifying or suspending a powdered plant-based dye together with liquid silicone, paraffins, a plant or animal oil using a surfactant or the like. Though this hair dye has an improved agent stability as well as an enhanced functionality in terms of hair-dyeing operation, it has a relatively low hair-dyeing performance, a property which should be prioritized for a hair dye. Thus, this hair dye does not meet all of the requirements either.

The indigo plant has long been grown by mankind and has a long history of being used as a dye for dyeing fibers, a coloring agent for food, or a medicament such as a detoxifying agent or an antipyretic agent. Making use of the dye component of the indigo in dyeing hair may provide those who are sensitive to conventional hair dyes with the benefit of dyeing their hair without having troubles. Furthermore, the indigo dyes are free of irritation and damage to scalps and hair and give hair body and a new texture of hair, providing a hair-dyeing effect that suits hair color of the Japanese.

SUMMARY OF THE INVENTION

The present invention addresses the above-mentioned problem. Accordingly, it is a first object of the present invention to provide a new hair dye using a natural indigo plant which does not stain skins when spilt thereon and is, for example, capable of preventing white hair from turning yellowish and of dyeing hair with natural tone while hiding white hair and which provides long-lasting, durable colors. A second object of the present invention is to provide a hair-dyeing method of dyeing hair using such new hair dyes.

The hair dye according to the first aspect of the present invention uses indigo dyes, which have a long history of being used as dyestuff for fibers, for the purpose of dyeing hair. The dye has an excellent shelf stability, does not stain skins when spilt, and provides long-lasting, durable colors. The dye is advantageous in that it allows the people who are sensitive to conventional hair dyes and could not dye their hair to enjoy dyeing their hair. The dye is free of irritation and damage to scalps and hair and is capable of preventing white hair from turning yellowish and of providing hair with natural tone. Also, the dye provides hair with a new textile and provides a long-lasting color that suits the hair color of the Japanese.

In order to attain the above-mentioned objects, a first aspect of the present invention is a new hair dye comprising, as essential ingredients, (i) a formulation primarily composed of a dye component including indican derived from an indigo plant and (ii) a formulation primarily composed of a β-glucosidase enzyme component.

The hair dye according to the first aspect of the present invention uses indigo dyes, which have a long history of being used as dyestuff for fibers, for the purpose of dyeing hair. The dye has an excellent shelf stability, does not stain skins when spilt, and provides long-lasting, durable colors. The dye is advantageous in that it allows the people who are sensitive to conventional hair dyes and could not dye their hair to enjoy dyeing their hair. The dye is free of irritation and damage to scalps and hair and is capable of preventing white hair from turning yellowish and of providing hair with natural tone. Also, the dye provides hair with a new textile and provides a long-lasting color that suits the hair color of the Japanese.

A second aspect of the present invention is characterized in that, in the foregoing hair dye, the formulation (i) primarily composed of the dye component including indican derived from an indigo plant is one selected from the group consisting of a fresh indigo leaf β-glucosidase of which is inactivated, an extract solution which contains indican extracted from fresh indigo leaves and which has its β-glucosidase component inactivated, an indican-containing powder obtained by freeze-drying the indican-containing extract solution, an indican-containing formulation in which the fresh indigo leaves having their β-glucosidase component inactivated and/or the indican-containing extract solution and/or the indican-containing powder is carried by a carrier such as starch, cellulose, and silk powder, and a mixture thereof.

The hair dye according to the second aspect of the present invention, which uses the formulation (i) which is not only highly stable but can also be obtained easily and economically, has the same advantages as the hair dye according to the first aspect of the present invention. The dye has a further advantage that it can be manufactured more easily and economically.

A third aspect of the present invention is characterized in that, in the foregoing hair dye, the formulation (ii) primarily composed of the β-glucosidase enzyme component is one selected from the group consisting of a fresh indigo leaf, Enokitake (*Flammulina velutipes*), Shiitake (*Lentinus Edodes*), a young corn leaf, an apricot kernel, an almond, a β-glucosidase-containing extract solution extracted therefrom, and a mixture thereof.

The hair dye according to the third aspect of the present invention, which uses the formulation (ii) which is not only highly stable but can also be obtained easily and economically, has the same advantages as the hair dye according to the first aspect of the present invention. The dye has a further advantage that it can be manufactured more easily and economically.

A fourth aspect of the present invention Is characterized in that, in the foregoing hair dye, the formulation (ii)

primarily composed of the β-glucosidase enzyme component is one selected from the group consisting of a juice of a fresh indigo leaf, a β-glucosidase-containing powder obtained by freeze-dried fresh indigo leaves or juice thereof, and a mixture thereof.

The hair dye according to the fourth aspect of the present invention, which uses the component (ii) which is not only highly stable but can also be obtained easily and economically, has the same advantages as the hair dye according to the first aspect of the present invention. The dye has a further advantage that it can be manufactured more easily and economically.

A fifth aspect of the present invention is characterized in that, the foregoing hair dye further comprises another dye material selected from the group consisting of a natural plant dyestuff of gamene, curcuma, sappanwood, cochineal, logwood, henna, Castanea (chestnut tree), *Allium cepa* (onion) or coffee, an extract thereof, a powder obtained by freeze-drying the extract, and a mixture thereof.

The hair dye according to the fifth aspect of the present invention can provide widened variation in colors, since it contains other dye materials as described above.

A sixth aspect of the present invention is characterized in that, the foregoing hair dye further comprises, as a bulking filler or as an excipient, a plant-based component derived from a plant selected from the group consisting of a tea leaf, comfrey, kamille, chlorella, rosemary, seaweed, and a mixture thereof.

The hair dye according to the sixth aspect of the present invention can provide an increased quantity by adding a plant-based component as described above.

A seventh aspect of the present invention is characterized in that, the foregoing hair dye further comprises, as a hair-dyeing conditioner, a saponin-containing plant-based component selected from the group consisting of *Sappindus Mukurossi Gaertn., Gleditschia Japonica Mig., Quillaia Saponaria Molina* and a mixture thereof.

The hair dye according to the seventh aspect of the present invention can suppress the formation of indirubin to allow the expression of the natural indigo color, since it contains, as a hair-dyeing conditioner, saponin-containing plant-based components as described above. One can pursue widened variation of colors, such as reddish purple added to the natural indigo color, by choosing the kinds of the saponin-containing plants used and by varying their amounts to be added.

An eighth aspect of the present invention is characterized in that, the foregoing hair dye further comprises a plant-based thickener including guar gum and purified extracts of seaweed, or an animal-based thickener including a silk protein in order to enhance the adhesive power to hair as well as the ability in hair-dyeing operation.

The hair dye according to the eighth aspect of the present invention has an advantage that, since the dye contains plant-based thickeners as described above, the dye can be conditioned so that it adheres well to hair, preventing the dye from dripping down when applied to hair. This improves the ability in hair-dyeing operation.

A ninth aspect of the present invention is characterized in that, the foregoing hair dye further comprises a naturally occurring or chemically synthesized additive including an oil, a conditioner, a surfactant, a humectant, and a mixture thereof, in order to provide hair with an enhanced texture.

The hair dye according to the ninth aspect of the present invention can provide hair with an enhanced texture, since the hair dye contains naturally occurring or chemically synthesized additives as described above.

A tenth aspect of the present invention is characterized in that, the foregoing hair dye further comprises an additive selected from the group consisting of an antiseptic or germicide such as parabens and benzoates, an anti-oxidant, a UV-absorbing agent, a chelating agent, and a mixture thereof, in order to achieve improved long-term stability.

The hair dye according to the tenth aspect of the present invention can achieve improved long-term stability, since the dye contains additives as described above.

An eleventh aspect of the present invention is a hair-dyeing method comprising the steps of: mordanting hair with a dye mordant selected from the group consisting of a metal element of aluminum, iron, zinc, nickel, calcium, or magnesium, a metal salt thereof, and a mixture thereof; uniformly applying any of the foregoing hair dyes, the afore-mentioned hair dye comprising the formulation (i) primarily composed of the dye component including the indican derived from an indigo plant and the formulation (ii) primarily composed of the β-glucosidase enzyme component, the hair dye being applied to hair either directly or after mixed with a proper amount of water; and, upon completion of hair-dyeing, finishing the hair by rinsing with water and drying.

The method according to the eleventh aspect of the present invention ensures firm dyeing of hair.

A twelfth aspect of the present invention is a hair-dyeing method comprising the steps of: uniformly applying any of the foregoing hair dyes, the afore-mentioned hair dye comprising the formulation (i) primarily composed of the dye component including the indican derived from indigo plants and the formulation (ii) primarily composed of the β-glucosidase enzyme component, the hair dye being applied either directly or after mixed with a proper amount of water; upon completion of hair-dyeing, mordanting hair with a dye mordant selected from the group consisting of a metal element of aluminum, iron, zinc, nickel, calcium, or magnesium, a metal salt thereof, and a mixture thereof; and finishing the hair by rinsing with water and drying.

The method according to the twelfth aspect of the present invention ensures firm dyeing of hair.

BRIEF DESCRIPTION OF THE DRAWING

FIGURE illustrates the principle of color expression in hair-dyeing using indigo plants.

DETAILED DESCRIPTION OF THE PREFERRED EMBODIMENTS

The present invention will now be described in detail with reference to the accompanying drawing.

Examples of the plant from which indigo dyestuff of the present invention is made include, but are not limited to, those belonging to the genus indigofera including *Polygonum tinctorium, Strobilanthes cusia, Indigofera tinctoria*, and *Isatis indigotica*.

*Polygonum tinctorium* LOUR is an annual plant which belongs to the family Polygonaceae and is found in Indonesia, China and Japan.

*Strobilanthes cusia* (NEES) is a perennial plant belonging to the family Acanthaceae and is found in China and Okinawa.

*Indigofera tinctoria* is a perennial plant belonging to the family Leguminosae. It grows in countries such as India and Java.

*Isatis indigotica* FORTUNE is an annual plant belonging to the family Curciferae, and grows in the middle Europe and China.

Preferably, leaves of the indigo plants are used although the whole plant including roots and stems may also be used. The top leaves in growth are particularly suitable for use, though the leaves harvested for the first time or the third time of the year may also be used.

The figure shows the principle of how colors are expressed in hair-dyeing using the indigo plants.

As shown in the figure, indican (1) (water-soluble), which is a glucoside contained in the indigo plants principally in their leaves, is hydrolyzed by β-glucosidase, an enzyme which co-exists with the indican in the same plant, to form indoxyl (2) (water-soluble). The indoxyl (2) undergoes an oxidative dimerization to form indigo (3) (water-insoluble), which expresses colors.

For example, when a juice obtained by squeezing fresh indigo leaves is immediately applied to hair, hair-dyeing is accomplished in the following manner: Since the juice of fresh indigo leaves contains both indican (1) and the enzyme (β-glucosidase), indican (1) is hydrolyzed by the enzyme (β-glucosidase) to form indoxyl (2). The resulting indoxyl (2) penetrates into hair. When exposed to air, indoxyl (2) is oxidized and dimerizes to form indigo (3). This dyes the hair.

A drawback of this approach is that the chemical reaction as described above may proceed while the juice of indigo fresh leaves is stored, since the juice contains both indican (1) and the enzyme (β-glucosidase). This leads to reduced long-term stability.

The present invention is based on the discovery that the undesirable proceeding of the above-described reaction while the juice is stored can be avoided, for example, by separating (i) a dye component including indigo plant-derived indican, and (ii) an enzyme component, i.e., β-glucosidase, from the juice of fresh indigo leaves containing indican (1) and the enzyme (β-glucosidase), and then making each component into an individual formulation so that the two formulations are mixed together upon use to dye hair.

In the present invention, Examples of the formulation primarily composed of the dye component (i) including indican (1) derived from indigo plants include fresh indigo leaves in which the enzyme (β-glucosidase) is inactivated, or indican-containing extracts extracted from fresh indigo leaves in which the enzyme (β-glucosidase) is inactivated.

The enzyme (β-glucosidase) may be inactivated by heat-treating the fresh indigo leaves or the juice thereof, which contain the enzyme (β-glucosidase), for example, at a temperature from 60° C. to 100° C. for 3 to 60 minutes.

Fresh indigo leaves having the enzyme (β-glucosidase) inactivated may easily be obtained by heat-treating or steaming the fresh indigo leaves with the above-mentioned heat-treating conditions, by treating the leaves in a microwave, or by drying the leaves by sunlight.

Indican-containing extracts having the enzyme (β-glucosidase) inactivated may be obtained by extracting it from fresh indigo leaves in warm water in the temperature range mentioned above, or boiling, steaming, or microwaving the juice containing the enzyme (β-glucosidase) extracted from fresh indigo leaves in cold water, in the aforementioned temperature range.

In the present invention, the formulation primarily composed of the dye component (i) containing indican derived from indigo plants may be formed as an indican-containing powder obtained by freeze-drying, by a conventional method, the aforementioned indican-containing extracts having the enzyme (β-glucosidase) inactivated. Making the formulation into a powder is preferred since it ensures high shelf stability and easy-handling.

Also, in the present invention, the formulation primarily composed of the dye component (i) containing indican derived from indigo plants may be an indican-containing formulation in which the above-described fresh indigo leaves having the enzyme (β-glucosidase) inactivated, and/or, the above-described indican-containing extracts having the enzyme (β-glucosidase) inactivated, and/or, the above-descrived indican-containing powder having the enzyme (β-glucosidase) inactivated is/are carried on a carrier such as starch, cellulose, silk powder.

Further, the formulation primarily composed of the dye component (i) containing indican derived from indigo plants may be formed as an indican-containing powder obtained by freeze-drying the aforementioned indican-containing extracts, which have the enzyme (β-glucosidase) inactivated and which is carried on a carrier such as starch, cellulose, silk powder or the like.

In the present invention, Examples the formulation primarily composed of the β-glucosidase enzyme component (ii) are not limited to those derived from indigo plants but includes those derived from Enokitake (*Flammulina velutipes*), Shiitake (*Lentinus Edodes*), young corn leaves, apricot kernels, almonds and the like, or β-glucosidase-containing extracts extracted therefrom.

In the present invention, however, the formulation primarily composed of the β-glucosidase enzyme component (ii) is preferably fresh indigo leaves or a juice thereof, or a β-glucosidase-containing powder obtained by freeze-drying fresh indigo leaves or a juice thereof.

Fresh indigo leaves or a juice of the fresh indigo leaves may be used as the above-described formulation primarily composed of β-glucosidase enzyme component (ii) since they contain both indican (1) and the enzyme (β-glucosidase), as described above.

In case of the fresh indigo leaves, the indican (1) present in the leaves would not be hydrolyzed by the enzyme (β-glucosidase) unless the leaves are beaten or smashed, while the juice of the fresh indigo leaves is susceptible to hydrolysis by the enzyme (β-glucosidase). Therefore, the juice of the fresh indigo leaves is preferably used by freeze-drying it into an enzyme (β-glucosidase) containing powder by a known method. The indican (1) in the enzyme (β-glucosidase) containing powder is not hydrolyzed by the enzyme (β-glucosidase) since no water is present in the powder. This ensures high shelf stability.

The formulation composed primarily of the dye component (i) including the indican derived from indigo plants, or the formulation composed primarily of the β-glucosidase enzyme component (ii) is preferably encapsulated in bags made of a multi-layered plastic film impermeable to water and oxygen or in glass containers, for the purposes of storage and transportation. The encapsulated formulations are stored until use when the seal is broken.

When the hair dye according to the present invention is used to dye hair, the formulation composed primarily of the dye component (i) including the indican derived from indigo plants and the formulation composed primarily of the β-glucosidase enzyme component (ii) are mixed to be uniformly applied to hair. The mixture may be applied directly onto hair, or alternatively, the mixture may further be mixed with a proper amount of water for application. Indican (1) is hydrolized by the enzyme (β-glucosidase) to form indoxyl (2). The resulting indoxyl (2) penetrates into hair. When exposed to air, the indoxyl (2) is oxidized and dimerizes to form indigo (3). Not only does this enable to dye hair in a desired dark color but also ensures highly durable hair-dyeing. After dyeing is completed, the hair is rinsed with water and is finished by drying.

The hair dye according to the present invention may be used alone, or another hair dyeing material may preferably be added to provide variation in colors.

Examples of the other hair dyeing material include gamene, *Quercus glauca*, *Prunus armeniaca* (apricot), *Rubia muneet*, *curcuma*, *Prunus mume* (plum), *Sophora japonica*, *Bruguiera gymnorriza*, *Diospyros kaki*, *Quercus dentata*, *Arthraxon hispidus*, *Chaenomeles sinensis*, *gambier*, *Phellodendron amurense*, *Osmanthus fragrans var. aurantiacus*, *Clerodendoron trichotomum*, *Cinnamonum camphora*, *Gardenia jasminoides*, *Quercus acutissima*, *Castanea* (chestnut tree), *Phyllostachys nigera var. nigera*, *Morus*, *Zelkova serrata*, *Laurus nobilis*, *Geranium nepalense subsp. thunbergii*, tea, coffee, cochineal, *Quercus serrata*, Japanese gall (*Melaphis chinensis*), *Viburnum erosum*, *Arthraxon hispidus*, *Prunus* (cherry), *Punica granatum*, *Chrysanthemum coronarium*, Shirakashi (Japanese name), sappanwood, *Malus sieboldii*, *Rubia tinctorum*, *Ilex pedunculosa*, *Machilus tunbergii*, *Allium cepa* (onion), *Daphne genkwa*, *Houttuynia cordata*, Japanese cinnamon, *Cornus florida*, *Erigeron philadelphicus*, *Arachis hypogea* (peanut), *Eribotrya japonica*, *Areca catechu*, *Pegucatechu*, *Carthamus tinctorius*, *Tagetes erecta* (Marigold), *Cornus controversa*, myrobalan, *Aphananthe aspera*, gromwell (Boraginaceae), *Alnus firma* Sieb. et Zucc., *Boehmeria longispica*, *Cornus kousa*, *Myrica rubra*, *Artemisia princeps*, lac, green tea, logwood, and mixtures of more than two of them.

Of these, natural plant dyes of gamene, curcuma, sappanwood, cochineal, logwood, henna, Castanea (chestnut tree), *Allium cepa* (onion), and coffee may preferably be used.

Dried and powdered portion of these plants including roots, stems, skins, leaves, flowers, fruits and seeds may be used. Also, an extract solution extracted using proper solvent or powdered extract may preferably be used. Examples of the solvent include water, alcohols having 6 carbons or less, polyols, benzene, chloroform, acetone, and ethers. These solvents may be used either individually or in combination of more than two.

Also, a plant-based component derived from plants such as aloe, kamille, licorice, chlorella, comfrey, cinnamon, shiitake, jasmine, sage, carrot, garlic, tea, peppermint, Marigold, lavender, rosemary, and seaweeds may be added in a proper amount as a bulking filler or an excipient.

Among these plants, tea leaves, comfrey, kamille, chlorella, rosemary, or seaweed is preferably used.

Furthermore, a saponin-containing plant including *Sappindus Mukurossi Gaertn.*, *Gleditschia Japonica Mig.*, *Quillaia Saponaria Molina*, *Panax ginseng*, *Panax ginseng var. japonica*, *Platycodon grandiflorum* (Chinese bellflower), *Aralia elata*, *Sophora japonica*, senega, *Glycine max* (Soybean), licorice, or *Fatsia japonica* may be added to the hair dye of the present invention as a hair-dyeing conditioner.

As shown in the figure, in addition to the reaction pathway in which indican (1) is hydrolyzed by the enzyme (β-glucosidase) to form indoxyl (2) (water-soluble) which oxdatively dimerizes to form indigo (3) when exposed to air, there is another pathway in which indirubin (5) is formed via isatin (4). The amount of indirubin (5) produced may be increased depending on conditions under which hair is dyed. Since indirubin (5) has a reddish purple color, this may cause the blue or deep-blue color, which is the natural color of indigo, to diminish, making hair appear more reddish purple.

However, because the addition of the saponin-containing plant such as *Sappindus Mukurossi Gaertn.*, *Gleditschia Japonica Mig.*, *Quillaia Saponaria Molina* to the hair dye of the present invention can suppress the formation of indirubin (5) and hence increase the amount of indigo (3) produced, natural colors of indigo plants are well expressed.

Accordingly, when it is desired to dye hair in the natural colors of indigo plants, it is preferred to add the saponin-containing plant such as *Sappindus Mukurossi Gaertn.*, *Gleditschia Japonica Mig.*, or *Quillaia Saponaria Molina*, preferably, *Sappindus Mukurossi Gaertn.* The natural colors of indigo plants may be adjusted to a slightly reddish purple depending on the kind of the saponin-containing plant or the amount of the plant added. Also, it is possible to obtain widened variation in color.

*Sappindus Mukurossi Gaertn.* has long been used as a detergent and is known to have a strong ability to foam. Hence, the plant is believed to act to provide a large surface area due to the formation of bubbles and thus a large supply of air. This may enhance the oxidative reaction in which indoxyl (2) oxidatively dimerizes to form indigo (3).

The amount of the above-described saponin-containing plant added is not particularly limited, but typically in a range from 0.1 to 20.0 wt %, preferably from 1 to 5 wt %, with respect to the total amount of the hair dye. When the amount is less than 0.1 wt %, suppression of formation of indirubin (5) is low. When the amount is greater than 20.0 wt %, further increases in the suppression effect are hardly expected. Rather, the hair-dyeing performance may deteriorate.

A thickener may be added in a proper amount to the hair dye of the present invention in order to enhance the adhesive power to hair as well as the ability in hair-dyeing operation.

Examples of the thickener include a) natural, semi-synthesized, or synthesized water-soluble polymers, b) electrolytes such as sodium chloride, potassium chloride, and sodium sulfate, c) nonionic surfactants, and d) oils.

In the present invention, a plant-based thickener including guar gum and purified extracts of seaweed, or animal-based thickeners including silk proteins is preferably used.

Examples of the other thickeners which may be used in the present invention include thickeners composed of those selected from the group consisting of celluloses, alginates and polysaccharides, and in particular, one or a mixture of more than two thickeners selected from the group consisting of methyl celluloses, ethyl celluloses, hydroxyethyl celluloses, methylhydroxyethyl celluloses, methylhydroxypropyl celluloses, carboxymethyl celluloses, polyvinylalcohol, carboxy vinyl polymers, alginic acid, sodium alginate, ammonium alginate, calcium alginate, gum arabic, xanthan gum, carrageenan, and cationic derivatives thereof. Preferably, the amount of the thickener to be added is from about 0.1 to about 15 wt %, and in particular, from about 0.2 to about 10 wt %.

Also, naturally occurring or chemically synthesized additives including oils, conditioners, surfactants and humectants may be added in a proper amount to the hair dye of the present invention in order to better texturize hair.

Examples of the additive which may used in the present invention include animal or plant-based fats and oils such as lanolin, mink oil, horse oil, almond oil, castor oil, jojoba oil, medford oil, and olive oil; animal or plant-based sterols such as cholesterin, lanolin alcohol, phytosterols and derivatives thereof; mineral, animal or plant-based waxes such as solid paraffin, ceresin, spermaceti wax, beewax, and carnauba wax; hydrocarbon oils such as liquid paraffin and squarane; higher alcohols such as lauryl alcohol, cetanol, cetostearil alcohol, and oleyl alcohol; higher fatty acids such as lauric acid, stearic acid, and oleic acid; synthetic oils such as polyoxyethylene polyoxypropylene glycol, isopropyl myristate, isopropyl palmitate, cetostearil isooctate, alkyl esters of isostearic acid; surfactants such as polyoxyethylenealkylether sulfate, 2-alkyl-N-carboxymethyl-N-hydroxyethyl imidazolinium betaine, and N-coconut fatty acid acyl-L-glutamate; surfactants such as higher alcohol polyoxyethylene ethers, higher fatty acid polyoxyethylene esters, hardened castor oil polyoxyethylene; polyols such as glycerol, sorbit, propylene glycol, 1,3-butylene glycol; lower alcohols such as ethanol; moisturizers such as hyaluronates, pyrrolidone carboxylate, hydrolyzed collagen, hydrolyzed keratin, hydrolyzed silk, and trehalose; and cationizing agents such as alkyltrimethylammonium chloride and cationized dextran.

The conditioner is added for the purposes of 1) preventing frizzy hair to assure smooth combing, 2) always keeping hair moist and soft for easy taming and long-lasting curls, 3) adding body and shine to hair, and 4) strengthening the hair.

Further additive selected from a germicide and/or an antiseptic such as parabens and benzoates, an anti-oxidant, a UV-absorbing agent, and a chelating agent may be added to the hair dye of the present invention in an proper amount that does not affect the desired effects of the hair dye of the present invention. The amount of the additive to be added is not limitative, but preferably in a range from 0.01 to 1.0 wt % with respect to the total amount of the hair dye. When the amount is less than 0.01 wt %, the long-term stability may not be obtained. Conversely, further improvement in the long-term stability is hardly expected and the hair dye may become costly when the amount exceeds 1.0 wt %.

Examples of the germicide and antiseptic which may be used in the present invention include acids such as benzoic acid, salicylic acid, dehydroacetic acid, and sorbic acid and salts thereof, sodium banzoate, oxybenzoic acid alkyl esters, cetylpyridinium chloride, benzalkonium chloride, alkyltrimethylammonium chloride, phenoxyethanol, triclosan, trichloro carbanilide, zinc pyrithione, and ethanol. Typically, use of two or more germicides or antiseptics in combination is effective.

Examples of the chelating agent (metal blocking agent) which may be used in the present invention include ethylenediaminetetraacetic acid derivatives, tripolyphosphate, hexametaphosphate, dihydroxyethylglycine, citric acid, tartaric acid, gluconic acid, and sugar acid. These agents act by forming complex salts with trace amounts of heavy metal ions.

Examples of the UV absorbing agent which may be used in the present invention include benzophenone derivatives such as oxybenzon, and benzatriazol derivatives.

The anti-oxidant used in the present invention is intended for preventing the hair dyes and hair dye compositions of the present invention from being oxidized. Examples of the anti-oxidant used herein including tocophenol, nordihydroguaiaretic acid, butylhydroxyanisole, dibutylhydroxytoluene, propyl gallate, sodium hydrogensulfite, erythorbic acid, parahydroxyanisole, extracts of tea, and extracts of apples may be used for this purpose.

A proper amount of perfumery may be added to the hair dye of the present invention. Perfumery is an important ingredient which, as well as colors, contributes to the products' attractiveness and increases the commodity values. It is also important in masking unpleasant odor of other ingredients.

One method for dyeing hair using the hair dye of the present invention includes first mordanting hair with a dye mordant including a metal element such as aluminum, iron, zinc, nickel, calcium and magnesium, or a metal salt thereof, and then uniformly applying the hair dye including the formulation primarily composed of the dye component (i) including the indican derived from indigo plants and the formulation primarily composed of the β-glucosidase enzyme component (ii). The formulations may be applied either directly or after mixed with a proper amount of water (for example, 10 to 200 g of water are mixed with 1 to 50 g of a mixture of the formulations (i) and (ii), and preferably, 50 to 150 g of water are mixed with 5 to 30 g of a mixture of the formulations (i) and (ii).) Hair-dyeing conditions are not particularly limited, but for example, hair-dyeing is carried out by leaving the hair for several to 30 minutes at about 40 to 45° C. After hair-dyeing is completed, the hair is rinsed with water and is finished by drying. Application of the dye mordant prior to the application of the hair dye provides more durable dyeing as compared to the hair-dyeing without the pre-application of the dye mordant.

Another method for dyeing hair using the hair dye of the present invention includes uniformly applying the hair dye including the formulation primarily composed of the dye component (i) including the indican derived from indigo plants and the formulation primarily composed of the β-glucosidase enzyme component (ii). The formulations may be applied either directly or after mixed with a proper amount of water (for example, 10 to 200 g of water are mixed with 1 to 50 g of a mixture of the formulations (i) and (ii), and preferably, 50 to 150 g of water are mixed with 5 to 30 g of a mixture of the formulations (i) and (ii).) Hair-dyeing conditions are not particularly limited, but for example, hair-dyeing is carried out by leaving the hair for several to 30 minutes at about 40 to 45° C. Upon completion of hair-dyeing, the hair is treated with a dye mordant including a metal element such as aluminum, iron, zinc, nickel, calcium or magnesium, or a metal salt thereof.

Subsequently, the hair is rinsed with water and is finished by drying. Application of the dye mordant after the application of the hair dye provides more durable dyeing as compared to the hair-dyeing without the post-application of the dye mordant.

EXAMPLES

The present invention will now be described in further detail, however, it should be appreciated that the present invention is not limited to these examples.

Example 1

Fresh indigo leaves collected from the top portion of the growing indigo plants were extracted in hot water at a temperature of about 80 to 90° C. for about 10 to 20 minutes to prepare an extract solution in which the enzyme (β-glucosidase) had been inactivated. As a carrier, a cellulose powder was used to carry the extract, and the extract carried by the cellulose powder was freeze-dried to obtain an indican-containing formulation. A β-glucosidase-containing powder (i.e., enzyme (β-glucosidase) containing formulation) was prepared by freeze-drying crushed fresh indigo leaves. A hair dye according to the present invention was prepared by mixing 10.0 g of the indican-containing formulation, 1.0 g of the enzyme (β-glucosidase) containing powder, and 1.0 g of powdered extracts of *Sappindus Mukurossi Gaertn*. and dissolving the mixture into 100 ml of purified water. The dye was applied to hair, which was then wrapped in an appropriate manner, warmed to about 40 to 45° C. and left for 30 minutes. The hair was then dried and finished.

The hair dye of the present invention did not cause irritation or damage to scalps and hair, nor did it stain skins when spilt. Furthermore, the hair dye of the present invention was capable of preventing white hair from turning yellowish color and of dyeing hair with natural tone. It also showed high durability and provided hair with a new texture. The addition of the powdered extracts of *Sappindus Mukurossi Gaertn*. provided a darker blue.

Example 2

Fresh indigo leaves collected from the top portion of the growing indigo plants was extracted in hot water at a temperature of about 80 to 90° C. for about 10 to 20 minutes to prepare an extract solution in which the enzyme (β-glucosidase) had been inactivated. As a carrier, a cellulose powder was used to carry the extract, and the extract carried by the cellulose powder was freeze-dried to obtain an indican-containing formulation.

A β-glucosidase-containing powder (i.e., enzyme (β-glucosidase) containing formulation) was prepared by freeze-drying crushed fresh indigo leaves. A hair dye according to the present invention was prepared by mixing 10.0 g of the indican-containing formulation, 1.0 g of the enzyme (β-glucosidase)containing powder, 1.0 g of powdered extracts of *Sappindus Mukurossi Gaertn*., and 1.4 g of guar gum, and dissolving the mixture into 100 ml of purified water. The dye was applied to hair, which was then wrapped in an appropriate manner, warmed to about 40 to 45° C. and left for 30 minutes. The hair was then dried and finished.

The hair dye of the present invention did not cause irritation or damage to scalps and hair, nor did it stain skins when spilt. Furthermore, the hair dye of the present invention was capable of preventing white hair from turning yellowish color and of dyeing hair with natural tone. It also showed high durability and provided hair with a new texture. The addition of the guar gum enhanced the applicability of the dye and prevented the hair dye from dripping down.

Example 3

Hair-dyeing was carried out in the same manner as in Example 2 except that 5.0 g of powdered curcuma were used as an further additive.

The hair dye of the present invention did not cause irritation or damage to scalps and hair, nor did it stain skins when spilt. Furthermore, the hair dye of the present invention was capable of preventing white hair from turning yellowish color and of dyeing hair with natural tone. It also showed high durability and provided hair with a new texture. The addition of the powdered curcuma provided widened variation in color: A yellowish tone was added to the bluish tone, producing a greenish tone.

Example 4

Hair-dyeing was carried out in the same manner as in Example 3 except that 5.0 g of powdered henna were used in place of the powdered curcuma.

The hair dye of the present invention did not cause irritation or damage to scalps and hair, nor did it stain skins when spilt. Furthermore, the hair dye of the present invention was capable of preventing white hair from turning yellowish color and of dyeing hair with natural tone. It also showed high durability and provided hair with a new texture. The addition of the powdered henna provided widened variation in color: An orangeish tone was added to the bluish tone, producing a brownish tone.

Example 5

Hair-dyeing was carried out in the same manner as in Example 2 except that 3.0 g of powdered kamille were used as an further additive.

The hair dye of the present invention did not cause irritation or damage to scalps and hair, nor did it stain skins when spilt. Furthermore, the hair dye of the present invention was capable of preventing white hair from turning yellowish color and of dyeing hair with natural tone. It also showed high durability and provided hair with a new texture. The addition of the powdered kamille produced a grayish blue and provided an enhanced touch of the hair.

Example 6

Hair-dyeing was carried out in the same manner as in Example 2 except that 3.0 g of powdered seaweed were used as an further additive.

The hair dye of the present invention did not cause irritation or damage to scalps and hair, nor did it stain skins when spilt. Furthermore, the hair dye of the present invention was capable of preventing white hair from turning yellowish color and of dyeing hair with natural tone. It also showed high durability and provided hair with a new texture. The addition of the powdered seaweed provided enhanced shine and touch without sacrificing the indigo color.

Example 7

Hair-dyeing was carried out in the same manner as in Example 2 except that 3.0 g of powdered keratin were used as an further additive.

The hair dye of the present invention did not cause irritation or damage to scalps and hair, nor did it stain skins when spilt. Furthermore, the hair dye of the present invention was capable of preventing white hair from turning yellowish color and of dyeing hair with natural tone. It also showed high durability and provided hair with a new texture. The addition of the powdered keratin provided an increased resiliency as well as enhanced shine and touch without sacrificing the indigo color.

Example 8

Hair-dyeing was carried out in the same manner as in Example 2 except that 3.0 g of powdered silk were used as an further additive.

The hair dye of the present invention did not cause irritation or damage to scalps and hair, nor did it stain skins when spilt. Furthermore, the hair dye of the present invention was capable of preventing white hair from turning yellowish color and of dyeing hair with natural tone. It also showed high durability and provided hair with a new texture. The addition of the powdered silk provided an increased slip as well as enhanced shine and touch without sacrificing the indigo color.

In view of the results obtained by the Examples 5–8, it was determined that an enhanced touch of the dyed hair could be obtained by adding the additives such as a powdered plant, a hydrolyzed protein and the like.

While the presently preferred embodiments of the present invention have been shown and described, it will be understood that the present invention is not limited thereto, and that various changes and modifications may be made by those skilled in the art without departing from the scope of the invention as set forth in the appended claims.

What is claimed is:

1. A hair dye comprising, as essential ingredients, (i) a formulation composed of a dye component including an indican which is derived from an indigo plant and has been heat-treated to inactivate the natural β-glucosidase contained therein and (ii) a formulation composed of a β-glucosidase enzyme component.

2. The hair dye according to claim 1, wherein said formulation (i) composed of the dye component including indican is selected from the group consisting of a fresh indigo leaf which has been heat-treated to inactivate the natural β-glucosidase contained therein; an extract solution which contains indican extracted from fresh indigo leaves and has been heat-treated to inactivate the natural β-glucosidase contained therein; an indican-containing powder obtained by freeze-drying an indican-containing extract solution; an indican-containing formulation in which the fresh indigo leaves have been heat-treated to inactivate the natural β-glucosidase contained therein; an indican-containing extract solution; an indican-containing powder carried by a carrier selected from the group consisting of starch, cellulose, and silk powder; and mixtures thereof.

3. The hair dye according to claim 1, wherein said β-glucosidase enzyme component is selected from the group consisting of extract of a fresh indigo leaf, Enokitake (*Flammulina velutipes*), Shitake (*Lentinus Edodes*), a young corn leaf, an apricot kernel, an almond, and mixtures thereof.

4. The hair dye according to claim 1, wherein the formulation (ii) composed of the β-glucosidase enzyme component is one selected from the group consisting of a juice of a fresh indigo leaf, a β-glucosidase-containing powder obtained from freeze-dried fresh indigo leaves or juice thereof, and mixtures thereof.

5. The hair dye according to claim 1, further comprising another dye material selected from the group consisting of a natural plant dyestuff of gamene, curcuma, sappanwood, cochineal, logwood, henna, Castanea (chestnut tree), *Allium cepa* (onion) or coffee, an extract thereof, a powder obtained by freeze-drying the extract, and a mixture thereof.

6. The hair dye according to claim 1, further comprising, as a bulking filler or as an excipient, a plant-based component derived from a plant selected from the group consisting of a tea leaf, comfrey, kamille, chlorella, rosemary, seaweed, and a mixture thereof.

7. The hair dye according to claim 1, further comprising, as a hair-dyeing conditioner, a saponin-containing plant-based component selected from the group consisting of *Sappindus Mukurossi Gaertn., Gleditschia Japonica Mig., Quillaia Saponaria Molina* and a mixture thereof.

8. The hair dye according to claim 1, further comprising a plant-based thickener including guar gum and purified extracts of seaweed, or an animal-based thickener including a silk protein in order to enhance the adhesive power to hair as well as the ability in hair-dyeing operation.

9. The hair dye according to claim 1, further comprising a naturally occurring or chemically synthesized additive including an oil, a conditioner, a surfactant, a humectant, and a mixture thereof, in order to provide hair with an enhanced texture.

10. The hair dye according to claim 1, further comprising an additive selected from the group consisting of an antiseptic or germicide such as parabens and benzoates, an anti-oxidant, a UV-absorbing agent, a chelating agent, and a mixture thereof, in order to achieve improved long-term stability.

11. The hair dye according to claim 2, wherein:

the formulation (ii) composed of the β-glucosidase enzyme component is one seleted from the group consisting of extract of a fresh indigo leaf, Enokitake (*Flammulina velutipes*), Shitake (*Lentinus Edodes*), a young corn leaf, an apricot kernel, an almond, and mixtures thereof;

and further comprising:

another dye material selected from the group consisting of a natural plant dyestuff of gamene, curcuma, sappanwood, cochineal, logwood, henna, Castanea (chestnut tree), *Allium cepa* (onion) or coffee, an extract thereof, a powder obtained by freeze-drying the extract, and mixtures thereof;

as a bulking filler or as an excipient, a plant-based component derived from a plant selected from the group consisting of a tea leaf, comfrey, kamille, chlorella, rosemary, seaweed, and a mixture thereof;

as a hair-dyeing conditioner, a saponin-containing plant-based component selected from the. group consisting of *Sappindus Mukurossi Gaertn., Gleditschia Japonica Mig., Quillaia Saponaria Molina* and a mixture thereof;

a plant-based thickener selected from the group consisting of guar gum and purified extracts of seaweed, or an animal-based thickener in order to enhance the adhesive power to hair as well as the ability in hair-dyeing operation;

a naturally occurring or chemically synthesized additive selected from the group consisting of an oil, a conditioner, a surfactant, a humectant, and a mixture thereof, in order to provide hair with an enhanced texture;

an additive selected from the group consisting of an antiseptic or germicide, an anti-oxidant, a UV-absorbing agent, a chelating agent, and a mixture thereof, in order to achieve improved long-term stability.

12. The hair dye according to claim 2, wherein:

the formulation (ii) composed of the β-glucosidase enzyme component is one selected from the group consisting of a juice of a fresh indigo leaf, a β-glucosidase-containing powder obtained by freeze-dried fresh indigo leaves or juice thereof, and a mixture thereof;

and further comprising:

another dye material selected from the group consisting of a natural plant dyestuff of gamene, curcuma, sappanwood, cochineal, logwood, henna, Castanea (chestnut tree), *Allium cepa* (onion) or coffee, an extract thereof, a powder obtained by freeze-drying the extract, and a mixture thereof;

as a bulking filler or as an excipient, a plant-based component derived from a plant selected from the group consisting of a tea leaf, comfrey, kamille, chlorella, rosemary, seaweed, and a mixture thereof;

as a hair-dyeing conditioner, a saponin-containing plant-based component selected from the group consisting of *Sappindus Mukurossi Gaertn., Gleditschia Japonica Mig., Quillaia Saponaria Molina* and a mixture thereof;

a plant-based thickener selected from the group consisting of guar gum and purified extracts of seaweed, or an animal-based thickener in order to enhance the adhesive power to hair as well as the ability in hair-dyeing operation:

a naturally occurring or chemically synthesized additive selected from the group consisting of an oil, a conditioner, a surfactant, a humectant, and a mixture thereof, in order to provide hair with an enhanced texture;

an additive selected from the group consisting of an antiseptic or germicide, an anti-oxidant, a UV-absorbing agent, a chelating agent, and a mixture thereof, in order to achieve improved long-term stability.

13. The hair dye of claim 11 wherein said thickener is a silk protein.

14. The hair dye of claim 11 wherein said germicide is a parabens compound or a benzoate.

15. The hair dye of claim 12 wherein said thickener is a silk protein.

16. The hair dye of claim 12 wherein said germicide is a parabens compound or a benzoate.

* * * * *

UNITED STATES PATENT AND TRADEMARK OFFICE
CERTIFICATE OF CORRECTION

PATENT NO.   : 6,656,229 B1
DATED        : December 2, 2003
INVENTOR(S)  : Kazumi Taguchi et al.

It is certified that error appears in the above-identified patent and that said Letters Patent is hereby corrected as shown below:

Column 14,
Line 8, delete "the formulation (ii) composed of the".

Signed and Sealed this

Fourth Day of January, 2005

JON W. DUDAS
*Director of the United States Patent and Trademark Office*